United States Patent [19]
Schalkowsky

[11] Patent Number: 5,429,944
[45] Date of Patent: Jul. 4, 1995

[54] METHOD FOR TESTING THE COMPARATIVE EFFECT OF GROWTH-AFFECTING SUBSTANCES BY MULTIPLE DEPOSITIONS OF TEST MICROORGANISMS

[75] Inventor: Samuel Schalkowsky, Chevy Chase, Md.

[73] Assignee: Spiral System Instruments, Inc., Bethesda, Md.

[21] Appl. No.: 751,782

[22] Filed: Aug. 29, 1991

[51] Int. Cl.$^6$ .................... C12Q 1/00; C12Q 1/24; C12Q 1/02; C12Q 1/04
[52] U.S. Cl. ................................ 435/292; 435/4; 435/29; 435/30; 435/32; 435/287; 435/293; 435/809; 422/99
[58] Field of Search .................. 435/29, 34, 30, 293, 435/809, 32, 4, 287; 436/63; 422/99, 292

[56] References Cited

U.S. PATENT DOCUMENTS

| | | | |
|---|---|---|---|
| 3,799,844 | 3/1974 | Campbell et al. | 195/127 |
| 3,892,632 | 7/1975 | Campbell et al. | 195/103.5 R |
| 3,962,040 | 6/1976 | Campbell et al. | 195/127 |
| 4,514,495 | 4/1985 | Schalkowsky | 435/32 |

OTHER PUBLICATIONS

Wallace et al J. Microbiological Methods 10 (1989) 303–310.
"Laboratory Methods in Antimicrobial Chemotherapy", by David S. Reeves, Ian Phillips, J. David Williams, and Richard Wise, published by Churchill Livingstone 1978, pp. 8–30.
Spiral Plater Model D User Manual pp. 1–48 (undated).

*Primary Examiner*—Michael G. Wityshyn
*Assistant Examiner*—Jane A. Williams
*Attorney, Agent, or Firm*—Antonelli, Terry, Stout & Kraus

[57] ABSTRACT

A method for evaluating the comparative effect of growth-affecting substances, such as antimicrobial drugs or antibiotics, on different cultures of microorganisms is disclosed. The cultures are plated on the surface of a culture medium (12), such as agar, in adjacent at least partially separated tracks, such as tracks formed as Archimedes spirals. The cultures may be different concentrations of the same microbe or a test culture and a reference culture. The growth-affecting substances (22) are placed in contact with the culture medium on which the cultures have been plated preferably in the form of disks containing a powdered growth-affecting substance which dissolves and diffuses differentially into the culture medium to produce zones (24) of inhibition of growth extending radially outward from the disk. A comparison of the distance between the disk and the point of inhibition of the tracks of the different cultures which intersect the disk permits direct measurement of the comparative effects of the growth-affecting substance.

12 Claims, 2 Drawing Sheets

METHOD FOR TESTING THE COMPARATIVE EFFECT OF GROWTH-AFFECTING SUBSTANCES BY MULTIPLE DEPOSITIONS OF TEST MICROORGANISMS

TECHNICAL FIELD

The invention relates to the determination of the effect of growth-affecting substances (antimicrobial drugs or antibiotics) on the growth of microorganisms by means of the disk diffusion test and other tests which utilize a gradient of the substance to produce visible inhibition zones in a culture medium.

BACKGROUND ART

The agar disk diffusion test is the most widely used method in clinical laboratories, world-wide, for the evaluation of the ability of a growth-affecting substance (antimicrobial drugs or antibiotics) to inhibit the growth of infection-causing bacteria in samples obtained from body fluids or tissues of patients. The purpose of these tests is to select the drug for treatment most likely to facilitate control or eradication of the infection. With the disk diffusion test, a sample of the culture containing the organism to be tested is spread on the surface of an agar plate. Predetermined amounts of the various test drugs are contained, in powder form, in separate absorbent paper disks. The disks are placed on the surface of the agar previously inoculated with a test organism. During the subsequent period of incubation, the drug diffuses radially outward from the disk into the agar which forms a continuous radial gradient of drug concentration. At the same time, the organisms deposited on the surface utilize the nutrients provided in the agar to divide and, by virtue of their increasing numbers, to form a lawn of visible colonies in those areas of the plate where the presence of the drug does not inhibit their growth. Since inhibition is a function of drug concentration, the size of the inhibited area of growth, i.e. the circular region around the disk which is clear of visible colonies, becomes a measure of the ability of the drug to affect the growth of the test organism. The size of the zone of inhibition is thus used to characterize the degree of susceptibility or resistance of the test organism to a particular drug.

U.S. Pat. No. 4,514,495, which is assigned to the Assignee of the present invention, and a commercially available test known as the "E-Test", supplied by A. B. Biodisk, utilize visible inhibition zones to determine the effect of growth-affecting substances on the growth of microorganisms.

In the United Kingdom (and in some other countries) the decision as to the efficacy of a drug to inhibit growth of a test organism is made not in terms of the measured size of the zone of inhibition of the test organism. Instead, a comparison of the zone of inhibition of the test organism is made with the size of the zone produced by a reference organism having a response to the drug which is known. Such a comparison must be made under identical test conditions which requires that both the test and reference organisms be located on the surface of the same agar plate and subjected to the action of the drug from the same disk. This is accomplished by spreading the two organisms in separate but adjacent areas of the plate and placing the disk so that half of it is in the area of the reference organism and the other half in the area of the test organism. In other words, a line separates the two areas which bisects the disk. Two- half circle inhibition zones will be created which are compared in size to determine how the test organism responds relative to the known response of the reference organism. This method is known as the Stokes or the comparative disk diffusion test.

The comparative disk diffusion test can also be used to evaluate the effect of different concentrations of the same test organism on the ability of the drug to inhibit its growth. For example, some organisms produce a substance which inactivates the drug thereby making it less effective in its action against the organism. Higher concentrations of the organism being tested produce more of the inactivating substance and will create a smaller zone of inhibition. A comparative test in this case consists of using two different concentrations of the same organism to measure the relative size of the two-half circle zones produced from the same disk.

The comparative disk diffusion test, as currently practiced, requires that the disk be placed in a particular location on the agar plate so as to create the same gradient of drug concentrations in the two test areas. In addition, the comparison requires the measurement, or observation of two distinct zones of inhibition, in order to obtain the difference between them.

The prior art methods have the disadvantage of being predominately manually implemented. The deposition of the microorganism colonies is performed manually. Furthermore, it is necessary to accurately center the disk with respect to the boundary between two cultures. These manual steps can produce variation in the results. Furthermore, the manual deposition of the cultures does not permit a controllable gradient of the culture to be deposited on the culture medium. As a result, differential effects of the drug based upon different concentrations of the test organism may not be readily performed on the same culture medium.

DISCLOSURE OF INVENTION

The present invention is an improved method of evaluating the comparative effect of a growth-affecting substance on different cultures of at least one microorganism. In accordance with the invention, a plurality of cultures of at least one microorganism are deposited on a culture medium with each of the cultures being deposited as a plurality of adjacent tracks with the tracks of each culture being separated by a track of at least one other culture.

Preferably, the tracks of the different cultures are in the form of a spiral with the plurality of cultures each being deposited in a spiral having tracks separated by spiral tracks of at least one other culture. The starting point of each spiral is preferably displaced from the starting point of at least one other spiral by a number of degrees equal to 360°/n wherein n is the number of cultures which are deposited on the culture medium. The spiral cultures may be deposited onto the surface of an agar plate by an apparatus in accordance with U.S. Pat. Nos. 3,799,844, 3,892,632 and 3,962,040 which are incorporated herein by reference or by the SPIRAL PLATER ® which is a commercially available spiral plating device manufactured by Spiral Systems, Inc., 6740 Clough Pike, Cincinnati, Ohio 45244.

The rate of dispensing the cultures along each of the spirals is controllable. In practicing the invention to perform the current disk diffusion test, a uniform density lawn of test organisms is produced on the surface of the culture medium by depositing a concentration of organisms of each of the cultures in spirals with a constant number of organisms per unit area for each culture. The spiral cultures contact the growth-affecting substance where the growth-affecting substance is deposited on the surface of the culture medium and diffuses radially outward to form a gradient of decreasing concentration.

Fixed spacing between adjacent tracks of each spiral is adjustable by selection of the rate of rotation of a turntable holding the culture medium relative to the linear rate of motion of a dispensing stylus from which each of the cultures is deposited. Preferably, the spiral spacing between each of the tracks of a culture is sufficiently wide to accommodate adjacent non-overlapping spiral tracks of colonies produced by organisms of each of the other cultures to be utilized in the test. However, adjacent tracks of different cultures may partially overlap. A minimum of two cultures is utilized.

If organisms within each of the cultures are inhibited at different concentrations of the growth-affecting substance, the edge of a zone of inhibition on the culture medium produced after the deposited cultures are incubated to produce visible colonies will have a sawtooth shape when the tracks are spirals intersecting near the center of an area of contact of the growth-affecting substance with the culture medium. The difference in zone size between the adjacent tracks of each of the cultures is a direct measure of the difference in response of the cultures to the growth-affecting substance. If the transition from growth to no growth is not sharp, selected differences in the transition also serve to compare a differential effect of the growth-affecting substance on the different cultures.

The deposition of a plurality of tracks with a constant concentration of microbes within each culture per unit area on the entire surface of the culture medium permits the area of contact of the growth-affecting substance, which preferably is produced by the placement of a disk containing the growth-affecting substance in a dry powdered form as in the prior art disk diffusion test on the surface of the culture medium, to be positioned anywhere on the plate without geometrical constraints such as in the prior art where the disk of the growth-affecting substance had to be placed midway between depositions of first and second cultures. Furthermore, utilization of the aforementioned apparatus to produce spiral tracks of the cultures provides efficient space utilization of the entire surface of the culture medium. Substantial manual effort is not required to deposit the spiral tracks of the growth-affecting substance when the aforementioned apparatus are utilized.

A method of evaluating a comparative effect of a growth-affecting substance on different cultures of at least one microorganism in accordance with the invention includes depositing a plurality of cultures of at least one microorganism on a culture medium with each of the cultures being deposited as a plurality of adjacent tracks with the tracks of each culture being separated by a track of at least one other culture; placing a growth-affecting substance in contact with the deposited plurality of cultures at at least one area of contact on the culture medium to create a gradient of concentration of the growth-affecting substance on the surface of the culture medium; incubating the culture medium to produce visible microbial growth on the tracks of the cultures on the culture medium and a surface area of inhibited growth of microorganisms on the surface of the culture medium extending from the at least one area of contact of the growth-affecting substance on the surface of the growth-affecting substance; and comparing a distance extending from at least one area of contact of the growth-affecting substance of a plurality of tracks of different cultures intersecting the growth-affecting substance to points of interest on the surface area of the culture medium where inhibited microbial growth occurs for the plurality of tracks intersecting the area of contact of the growth-affecting substance to determine if the distances are different for tracks of the different cultures with the comparison of the distances providing a determination of a degree of growth inhibition of the growth-affecting substance for the cultures. The point of interest for at least one track of each culture intersecting the growth-affecting substance may be either a point of total inhibition or a point of partial inhibition. The tracks of each culture may be in different geometrical patterns such as, but not limited to, sections of a spiral or parallel lines. The cultures may be different concentrations of a single microorganism or different microorganisms. Each culture may be deposited with a constant concentration of microorganisms per unit area of the culture medium to produce a constant concentration of microorganisms at different locations of the culture medium or each culture may be deposited with a concentration per unit area of the culture medium which changes to produce a different concentration of microorganisms at different locations of the culture medium to permit a differential comparison of the effect of different concentrations of the growth-affecting substance.

BEST MODE FOR CARRYING OUT THE INVENTION

The present invention is a method of evaluating a comparative effect of a growth-affecting substance, such as an antibiotic, for determining the effectiveness of the growth-affecting substance in inhibiting growth of microbes contained in a plurality of cultures which have been deposited on a culture medium. Each of the cultures are deposited as a plurality of adjacent tracks with the tracks of each culture being separated by a track of at least one other culture. Preferably, the present invention is practiced in conjunction with an apparatus which is described in U.S. Pat. Nos. 3,799,844, 3,892,632 and 3,962,040 or the SPIRAL PLATER® manufactured by Spiral Systems, Inc. With the invention, the manual deposition of the prior art disk diffusion test and the attendant variation produced by manual plating of two cultures on the culture medium and the placement of a growth-affecting substance at the intersection of the cultures are eliminated. Furthermore, plating of the cultures in a preferred pattern of a spiral on a culture medium with each of the cultures being deposited as a plurality of adjacent tracks with the tracks of each culture being separated by a track of at least one other culture provides efficient space utilization of a culture medium plate. As a result, multiple areas of the culture medium plate may be efficiently used to test different growth-affecting substances or different concentrations of the same growth-affecting substance. Furthermore, programming of the rate of deposition of the cultures on the surface of the culture medium permits variation of the concentration of microorganisms of the cultures at different locations of the culture medium enabling examination of the differential effect of the growth-affecting substance at different concentrations of the growth-affecting substance on the same culture medium.

Figure 1:
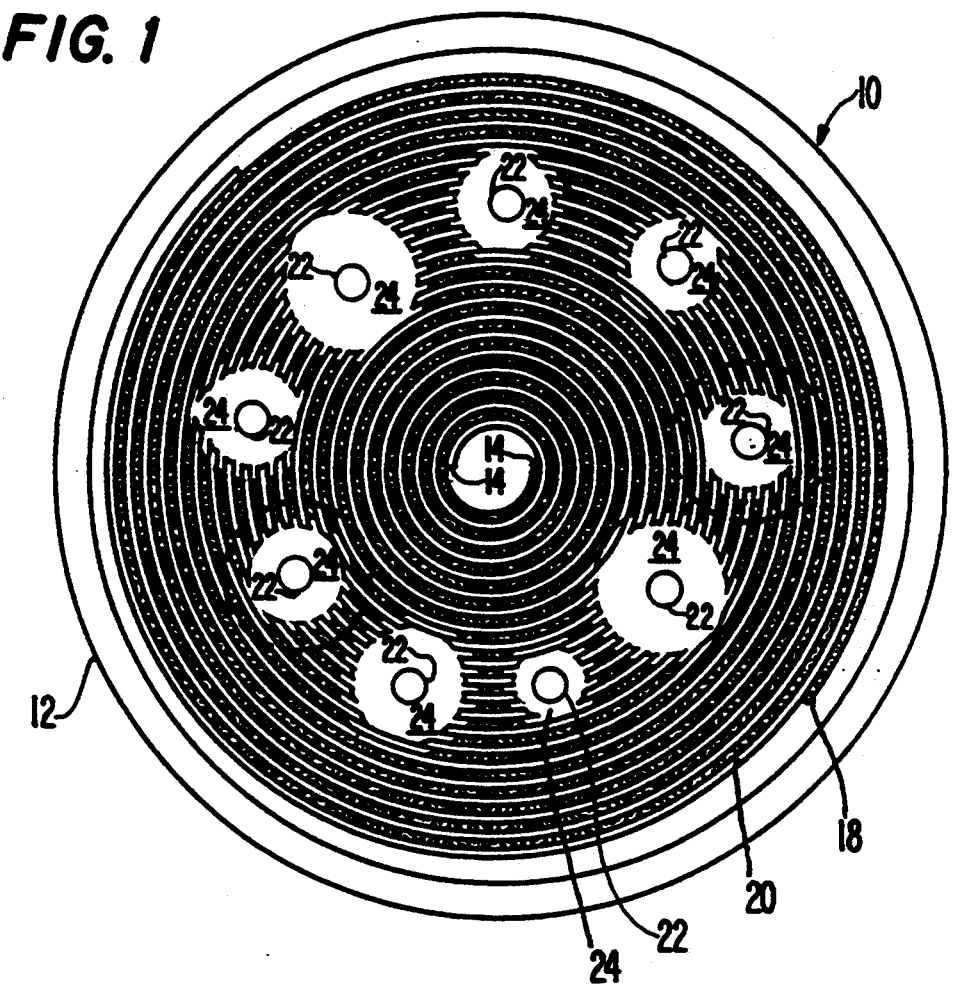
FIG. 1 illustrates an incubated plate of two cultures which have been plated on a culture medium to produce visible microbial growth to which has been applied a plurality of growth-affecting substances at different locations on the plate to produce a plurality of areas of inhibited growth.
Figure 2:
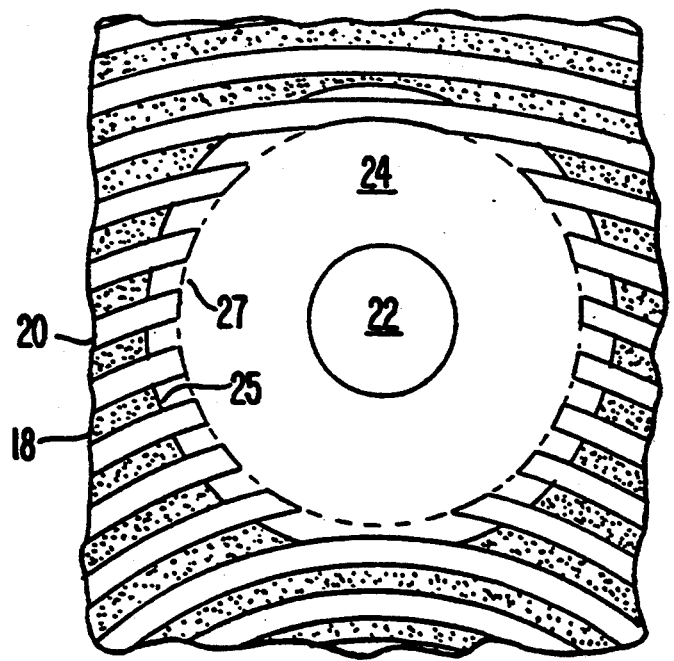
FIG. 2 is an enlargement of an inhibited area of growth in FIG. 1 illustrating a differential effect of the growth affecting substance on spiral tracks of first and second cultures.

FIG. 1 illustrates an incubated plate 10 of a commercially available culture medium plate 12. A plurality of cultures, which may contain either a single microorganism of different concentrations or different microorganisms, are plated to form adjacent tracks in a spiral with each of the cultures being deposited as a plurality of adjacent tracks with the tracks of each culture being separated by a track of at least one other culture. The starting points 14 of each of the plurality of cultures 18 and 20 are separated by a number of degrees equal to 360°/n wherein n is the number of cultures. Plating of the cultures in the spiral pattern, as illustrated in FIG. 1, is accomplished by rotating the starting point of each of the cultures through a number of degrees determined by the above-described formula. An apparatus in accordance with the above-referenced patents or the SPIRAL PLATER® manufactured by Spiral Systems, Inc. is utilized with each culture being plated successively by varying the starting point 14 at the center of the culture medium for each of the cultures being plated. For example, if three cultures were to be plated, the starting points 14 would be separated by 120° instead of 180° as illustrated in FIG. 1. Plating is accomplished by placing a sample of each of the cultures within a liquid carrier which is deposited under programmed control by the aforementioned apparatus to produce the spiral deposition as illustrated in FIG. 1. The programmed rate of deposition may be constant per unit area of the culture medium as illustrated in FIGS. 1-2 such that the concentration of the microorganisms in each of the cultures per unit area on the culture medium is constant throughout the geometrical surface area of the culture medium 12 or the programmed rate of deposition may be varied (not illustrated) with a programmed gradient as is conventionally produced by the aforementioned apparatus to produce a gradient of the concentration of the cultures per unit area which decreases in concentration with increasing radius of each of the cultures. When a gradient of the concentration of the cultures is utilized, differential effects of the growth-inhibiting substance may be examined by choosing the location of the surface area at which the growth-affecting substance contacts the culture medium 12 with locations which are spaced at an increased radius from the center of the plate having a smaller concentration of microorganisms in each of the cultures as a result of decreasing the volume of solution containing the cultures which is deposited per unit area as the radius of deposition measured from the center of the plate decreases. The actual concentration of the microorganism at each point of interest on the culture medium may be readily calculated as a function of radius given the programmed rate of deposition. Tables are available for determining the actual concentration given the distance from the center of the plate.

The deposition of a plurality of cultures 18 and 20 is completed with adjacent tracks of each of the cultures being separated by a track of the other culture on the culture medium. At the time of deposition, the cultures 18 and 20 do not have the visible colonies illustrated in FIG. 1. At least one type of growth-affecting substance 22 is placed in contact with the deposited cultures at at least one area of the culture medium 12. As illustrated in FIG. 1, a plurality of disk samples of different growth-affecting substances 22, such as those utilized in the prior art disk diffusion test, are applied at spaced apart locations on the culture medium to produce surface contact between the growth-affecting substances in the form of disks and the cultures 18 and 20 which have been deposited on the culture medium. When the aforementioned apparatus is used to deposit the cultures, the disks of the growth-affecting substance 22 are preferably placed in contact with the culture medium after the depositing of the cultures is completed. Typically, different growth-affecting substances 22 in the form of the disks are applied at different locations on the culture medium on which the cultures have been deposited. Incubation of the culture medium after the cultures have been deposited and the disks 22 of growth-affecting substance have been placed at at least one area of contact of the culture medium creates visible colonies of the microbes in the cultures and a zone of inhibition 24 which extends radially outward from the growth-affecting substance contained in the disks at which no visible microbial growth occurs as illustrated in FIG. 1. An area between the dotted line at which full microbial growth occurs and the circle at which no growth occurs for each culture 18 and 20 may occur which is a transition zone which may also be compared for each culture like the comparison of the distances from the growth-affecting substance to the point where visible growth first begins to occur for each culture. The dried growth-affecting substance 22 contained within each of the disks dissolves and diffuses into the culture medium to form a gradient of decreasing concentration of the growth-affecting substance 22 which extends on the surface area of the culture medium disks outward from the disks. The radius of the zone of inhibition 24 varies as illustrated in FIG. 1 between different areas of contact of the growth-affecting substance 22 with the culture medium 12. The comparison of the effectiveness of the growth-affecting substance or substances in inhibiting growth in the different cultures is performed with reference to individual areas of contact of a growth-affecting substance 22 as described below with reference to FIG. 2.

FIG. 2 illustrates an enlargement of a zone of inhibition 24 of the type illustrated above in FIG. 1. Like reference numerals identify like parts in FIGS. 1 and 2. The concentration of the growth-affecting substance 22 decreases radially outward as a function of increasing radius measured from the point of contact of the growth-affecting substance 22 with the culture medium. As is apparent in FIG. 2 for adjacent tracks of the cultures 18 and 20 which intersect the growth-affecting substance 22, the boundaries of inhibition of growth 25 and 27 of the cultures 18 and 20 occur at different concentrations of the growth-affecting substance which provides a comparative measure of the effectiveness of the growth-affecting substance independent of whether the cultures contain the same microorganism at different concentrations or different microorganisms. Specifically, a distance extending from the area of contact of a track of a culture intersecting the area of the growth-affecting substance 22 to where visible microbial growth for the track intersecting the area of the growth-affecting substance intersects the circular boundaries 25 and 27 of inhibited growth for the cultures 18 and 20 as illustrated in FIG. 2 is a measure of the effectiveness of the growth-affecting substance.

As illustrated in FIG. 2, the point of inhibition for the track 18 occurs farther from the area of contact of the growth-affecting substance 22 than the track 20 which provides a comparison of a degree of growth inhibition of the growth-affecting substance for the microbes within the cultures in the same way as the disk diffusion test of the prior art described above for the particular growth-affecting substance which is used. It is apparent from FIG. 2 that the growth-affecting substance 22 contained within the disk is more effective in inhibiting growth of the microbes contained within the culture 18 than the culture 20. This indication is the same type of indication as contained in the prior art disk diffusion test. Similarly, the relative width of transition zone (not illustrated) identified as a dotted line circle in FIG. 1 for one or more growth-affecting substances 22 between totally inhibited growth and full growth for each culture 18 and 20 may be compared when a visually significant transition zone is present for each culture.

It is thus seen that a comparison of the distances measured from the center of each growth-affecting substance 22 for at least one track intersecting the growth-affecting substance of each culture to a point of interest of inhibited growth is made to compare the effects of the growth-affecting substance on microbial growth. The points of interest for the tracks may be where total inhibition occurs, where the transition zone identified by the dotted line in FIG. 1 is located or a point between the dotted line and where inhibition occurs such as where a selected degree of full microbial growth (e.g. 50%) occurs.

The present invention may also be used to determine the differential effect of a growth-affecting substance 22 at different concentrations of the cultures produced by plating the cultures with a decreasing sample volume per unit area for increasing radial distance of a track measured from the center of the culture medium. Disks containing the same growth-affecting substance 22 at the same concentration may be placed at different radial positions with respect to the center of the culture medium so that the growth-affecting substance will contact different concentrations of the microbes in the cultures per unit area to test the differential effect of the growth-affecting substance as a function of the concentration of microbes per unit area.

Each of the methods described above involving the deposition of a constant concentration of microbes per unit area or a varying concentration of microbes per unit area may be practiced with the same microbe in different concentrations to form the plural cultures which are plated on the culture medium as described above or with a test microorganism forming one culture and a reference microorganism forming another culture to provide comparative effects of the growth-affecting substance on a known microorganism with an unknown microorganism.

Figure 3:
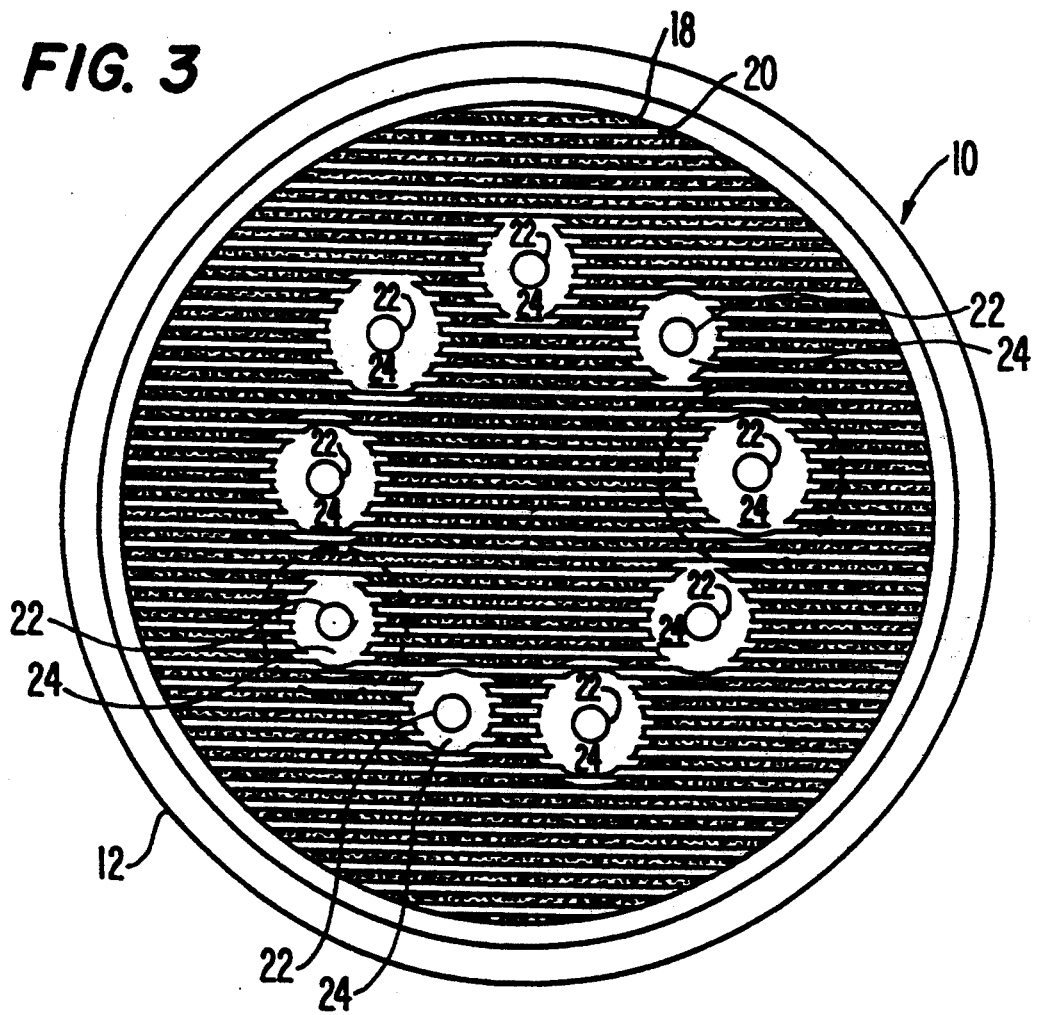
FIG. 3 illustrates an alternative geometric pattern of two cultures with tracks of the cultures being parallel lines.
Figure 4:
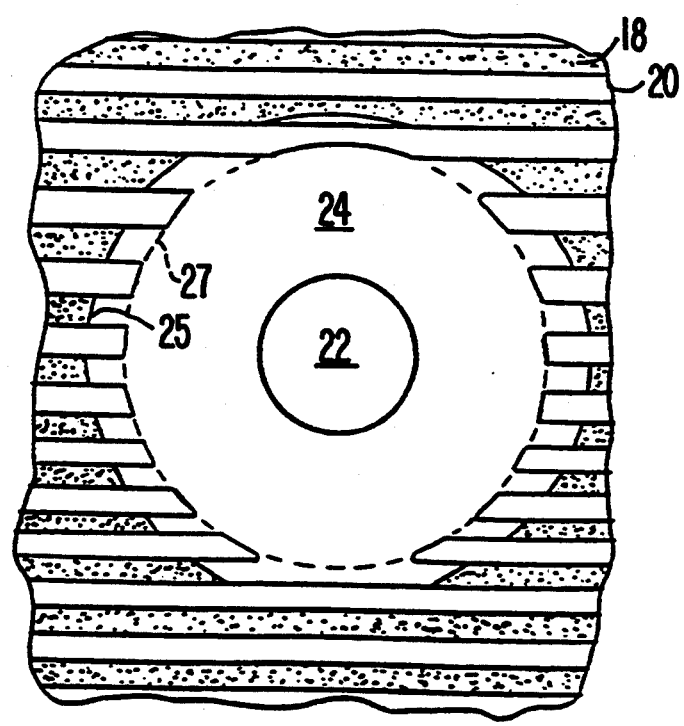
FIG. 4 is an enlargement of an inhibited area of growth in FIG. 3 illustrating a differential effect of the growth-affecting substance on parallel tracks of first and second cultures.

FIGS. 3 and 4 illustrate an alternative embodiment of the present invention in which the tracks of the cultures are in parallel lines. Like reference numerals identify like parts in FIGS. 1–4. The deposition to form the tracks of FIGS. 3 and 4 may be performed by displacing the culture medium or stylus depositing the cultures through rectilinear coordinates instead of rotation with a stylus moving with an increasing radius with respect to the center of the rotating culture medium as in accordance with the above-identified patents. It is important to note that the present invention is not limited to any particular geometrical pattern of the tracks of the plurality of cultures.

While the invention has been described in terms of its preferred embodiments, it should be understood that numerous modifications may be made thereto without departing from the spirit and scope of the invention as defined in the appended claims. It is intended that all such modifications fall within the scope of the appended claims.

I claim:

1. A method of evaluating a comparative effect of a growth-affecting substance on growth of different cultures of at least one microorganism on a solid culture medium comprising:

depositing a plurality of cultures on the culture medium with each of the cultures being comprised of a deposition on the culture medium containing at least one species of microorganism and the deposition of each culture being deposited as a plurality of adjacent tracks with the tracks of each culture having opposed sides facing adjacent tracks of a different culture;

placing a growth-affecting substance in contact with the deposited plurality of cultures at at least one area of contact on the culture medium so that the growth affecting substance diffuses into the culture medium and contacts a plurality of tracks of each of the plurality of cultures to create a gradient of concentration of the growth-affecting substance on the surface of the culture medium which extends outward from the at least one area of contact of the growth affecting substance with the culture medium;

incubating the culture medium to produce visible microbial growth on the tracks of the cultures on the culture medium and a surface area of inhibited growth of microorganisms on the surface of the culture medium extending from the at least one area of contact of the growth affecting substance outward from the at least one area of contact of the growth affecting substance to the visible microbial growth of the cultures on the surface of the culture medium; and comparing a distance extending outward from one of the at least one area of contact of the growth-affecting substance with the culture medium through the diffusion of the growth-affecting substance into the culture medium to an area of interest on the surface of the culture medium where inhibited microbial growth occurs for the plurality of tracks of each of the cultures contacting the diffusion of the growth-affecting substance into the culture medium to determine if the distances are different for tracks of each of the cultures contacting the diffusion with the comparison of the distances providing a measure of any differential effect on growth inhibition of the growth-affecting substance for the microorganisms within the cultures; and wherein the visible adjacent tracks of each culture are part of a spiral with each culture being deposited as a continuous spiral.

2. A method in accordance with claim 1 wherein:
the depositions of the cultures are different concentrations of a single species of microorganism.

3. A method in accordance with claim 1 wherein:
the depositions of the cultures are different species of microorganisms.

4. A method in accordance with claim 1 wherein:
each culture is deposited with a constant concentration of microorganisms per unit area of the culture medium to produce a constant concentration of microorganisms per unit area at different locations of the culture medium.

5. A method in accordance with claim 1 wherein:
each culture is deposited with a concentration per unit area of the culture medium which changes to produce a different concentration of microorganisms per unit area at different locations of the culture medium.

6. A method in accordance with claim 2 wherein:
each culture is deposited with a constant concentration of microorganisms per unit area of the culture medium to produce a constant concentration of microorganisms per unit area at different locations of the culture medium.

7. A method in accordance with claim 2 wherein:
each culture is deposited with a concentration per unit area of the culture medium which changes to produce a different concentration of microorganisms per unit area at different locations of the culture medium.

8. A method in accordance with claim 3 wherein:
each culture is deposited with a constant concentration of microorganisms per unit area of the culture medium to produce a constant concentration of microorganisms per unit area at different locations of the culture medium.

9. A method in accordance with claim 3 wherein:
each culture is deposited with a concentration per unit area of the culture medium which changes to produce a different concentration of microorganisms per unit area at different locations of the culture medium.

10. A method in accordance with claim 1 wherein:
the area of interest is where the growth of the microbes of the cultures is totally inhibited.

11. A method in accordance with claim 1 wherein:
the area of interest is where the growth of the microbes is partially inhibited.

12. A method in accordance with claim 1 wherein:
starting points for each of the continuous spirals are separated by a number of degrees equal to 360°/n wherein n is a number of cultures.

* * * * *